(12) United States Patent
Boswell

(10) Patent No.: US 8,023,108 B2
(45) Date of Patent: Sep. 20, 2011

(54) CRYSTALLOGRAPHIC ORIENTATION MEASUREMENT

(75) Inventor: John H. Boswell, Derby (GB)

(73) Assignee: Rolls-Royce PLC, London (GB)

(*) Notice: Subject to any disclaimer, the term of this patent is extended or adjusted under 35 U.S.C. 154(b) by 109 days.

(21) Appl. No.: 12/457,887

(22) Filed: Jun. 24, 2009

(65) Prior Publication Data

US 2010/0053596 A1 Mar. 4, 2010

(30) Foreign Application Priority Data

Sep. 4, 2008 (GB) .................................. 0816047.5

(51) Int. Cl.
G01N 21/00 (2006.01)

(52) U.S. Cl. ......................................................... 356/30

(58) Field of Classification Search .................. 356/300, 356/30
See application file for complete search history.

(56) References Cited

U.S. PATENT DOCUMENTS

| 4,548,255 | A | 10/1985 | Reiner et al. |
| 4,747,684 | A * | 5/1988 | Weiser ............................. 356/31 |
| 5,589,690 | A | 12/1996 | Siewert et al. |
| 2002/0005952 | A1 | 1/2002 | Sugai et al. |
| 2006/0268283 | A1 * | 11/2006 | Luezas et al. ................. 356/600 |

FOREIGN PATENT DOCUMENTS

| DE | 197 25 535 A1 | 12/1998 |
| EP | 1 494 275 A1 | 1/2005 |

* cited by examiner

Primary Examiner — Tarifur Chowdhury
Assistant Examiner — Abdullahi Nur
(74) Attorney, Agent, or Firm — Oliff & Berridge, PLC

(57) ABSTRACT

A method is disclosed for measuring the crystallographic orientation of a component cast by a directional solidification process. The method comprises the steps of: illuminating at least a region of the component surface with substantially coherent light, measuring the mean angle and intensity of the light reflected from the component surface, and correlating said mean angle and intensity to the crystallographic orientation of the component. The method has been found to lend itself particularly well to automation.

10 Claims, 3 Drawing Sheets

CRYSTALLOGRAPHIC ORIENTATION MEASUREMENT

The present invention relates to the measurement of crystallographic orientation in cast components, and more particularly relates to a method of measuring the crystallographic orientation of a component cast by a directional solidification process.

Directional solidification can be used to produce cast components, such as turbine blades, nozzle guide vanes (NGVs), seal-segments or the like, for use in gas turbine engines. An advantage of a directionally solidified structure is that grain boundaries can be aligned appropriately with regard to the shape of the component (eg along the length of a turbine blade), providing increased creep strength at the high operating temperatures and stresses to which such components are typically exposed during operation of a gas turbine engine. Directional solidification can also be used to advantage in improving low cycle fatigue properties and blade vibration resonant frequencies. Crystal orientation can be controlled so as to avoid the cross-over of certain resonances.

In order to maximize these advantageous properties arising from direction solidification, it is therefore important to monitor closely the crystallographic orientation of such components so that any components falling below standard can be rejected before they are installed in the engine.

It has been proposed previously to measure primary crystallographic orientation by using x-ray diffraction, which involves firing x-rays into a component held in a fixture and measuring the diffraction pattern arising from the crystal lattice. However, this method suffers from a number of disadvantages, including the need for it to be performed by a highly trained and skilled operator, and the fact that only one component can be measured at a time which makes automation of the method impractical. Also, although the x-ray diffraction method is generally applicable to components having relatively simple shapes such as turbine blades, it can be difficult to implement on more complex shapes such as NGV components. Of course, using x-rays also involves working with radioactive material, with all of the consequent health and safety issues that go with that.

Creep strength in cast components can be increased still further by casting blades as single crystals in which there are no grain boundaries. In practice, however, it has been found that acceptable results can be achieved from components having secondary grains up to an acceptable limit, and so it is desirable to be able to conveniently detect the presence of high angle grain boundaries on single crystal components. This is presently done visually by trained technicians and so it would be advantageous to be able to do this by conveniently measuring the crystallographic mis-orientation between two crystal grains on a single crystal component. Secondary grains are currently thought to be acceptable in such components, up to a limit of approximately 8-10°, depending upon the actual component in question. It has been found that components can have larger mis-alignment between crystal grains in certain non-critical areas.

It is an object of the invention to provide an improved method for measuring the crystallographic orientation of a component cast by a directional solidification process.

Accordingly, a first aspect of the invention provides a method for measuring the crystallographic orientation of a component cast by a directional solidification process, the method comprising the steps of: illuminating at least a region of the component surface with substantially coherent light, measuring the mean angle and intensity of the light reflected from the component surface, and correlating said mean angle and intensity to the crystallographic orientation of the component. The invention thus provides a method of measuring the crystallographic orientation of a cast component via interferometry.

The step of measuring preferably comprises the use of an optoelectronic device arranged such that said light reflected from the component surface falls incident upon the optoelectronic device. The optoelectronic device may comprise a photodetector such as a photocell or other semi-conductor device, and may be electrically connected to a processor configured to perform the correlating step of the method.

The method preferably comprises the additional step of etching at least said region of the component surface prior to the step of illuminating the region, so as to expose the dendrite structure of the component in said region. It has been found that when the light reflected from the etched surface of the component, has an interference pattern which depends on, and hence is characteristic of, the orientation of the dendrites exposed by the step of etching. Because the dendrites are aligned with the crystal orientation of the component (ie the <001> crystallographic directions), then angle and intensity of the reflected light has been found to be dependant upon the crystallographic orientation of the component.

Preferably said step of etching involves electrochemical etching.

The method also preferably includes the step of substantially collimating the light incident on the component.

A laser device may used as the source of said substantially coherent light. A beam emitted from the laser is preferably directed through a diverging lens and then through a collimator before falling incident on the component surface. However, it should be appreciated that in an alternative arrangement a single laser beam could be used without the need to be directed through a collimator.

According to another aspect of the invention, there is provided a method of measuring the crystallographic orientation of a plurality of components cast by a directional solidification process, the method being substantially automated and comprising the step of successively presenting each said component for measurement in accordance with the method defined above.

The step of successively presenting preferably comprises successively moving the components to a predetermined measuring location using a conveyor or carousel arrangement.

Such a method can further comprise the step of comparing the measured crystallographic orientation to a predetermined range of acceptable values, and rejecting any component having a crystallographic orientation outside said range.

So that the invention may be more readily understood, and so that further features thereof may be appreciated, embodiments of the invention will now be described, by way of example, with reference to the accompanying drawings in which.

Figure 1A:
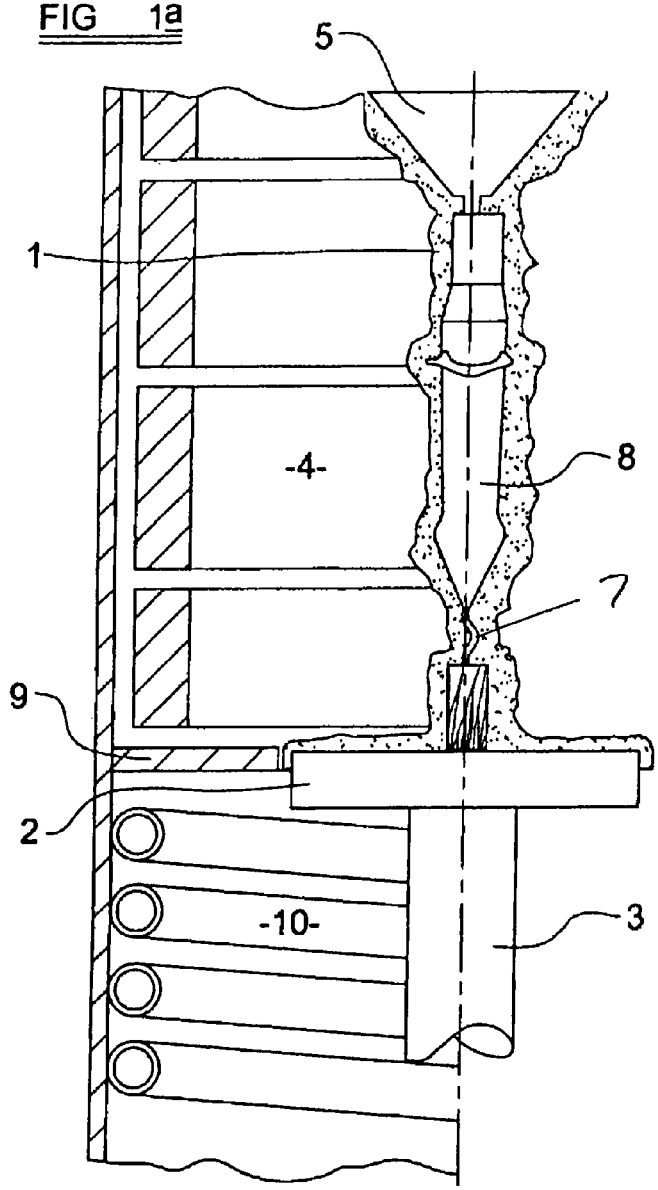
FIG. 1(a) shows schematically a cross-section through a directional solidification single crystal furnace.

Before turning specifically to consider the method of the present invention, it is relevant first to consider the method by which components such as turbine blades, NGVs, seal segments and the like are cast. Accordingly, FIG. 1(a) shows schematically a cross-section through a directional solidification single crystal furnace.

A ceramic mould 1 is positioned on a copper chill plate 2, itself installed on a hydraulic or motor-driven ram 3. The furnace is then sealed and evacuated. When a predetermined level of vacuum is reached, the ram is actuated to raise the mould into a resistance heated chamber 4, and the mould is allowed to soak. A charge of molten metal is then poured into the mould using a pour cup 5.

Figure 1B:
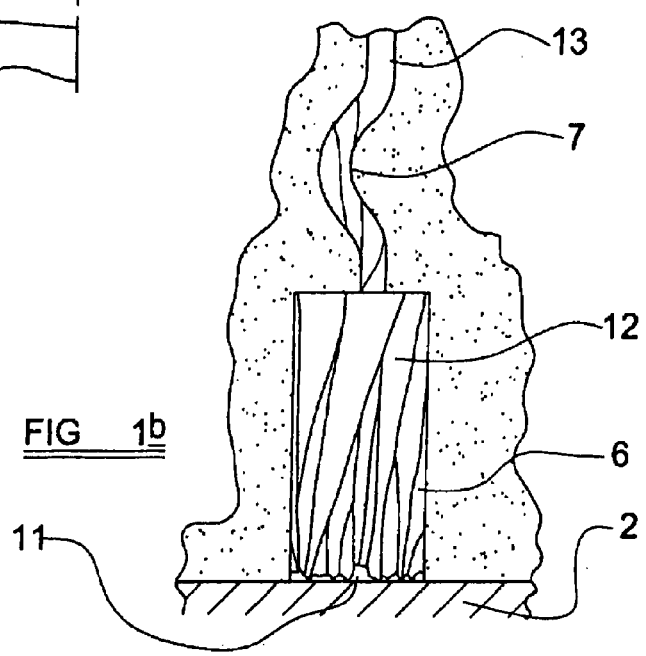
FIG. 1(b) shows a close up view of a portion of the single crystal furnace shown in FIG. 1(a)

FIG. 1(b) shows schematically a close up of the chill plate 2, and a base portion of the mould cavity.

The metal solidifies to form chill crystals 11 on the surface of the chill plate 2. The chill plate sets up a thermal gradient causing heat to flow in the direction from the heated chamber to the chill plate, and after a short period the chill crystals with the most favourable crystallographic orientations begin to grow epitaxially as columnar grains 12 in the direction opposite to the heat flow direction to form a starter block 6 of solidified metal at the base portion of the mould cavity.

Above the base portion of the mould cavity, the mould has a grain selector spiral 7, which is a helical passage connecting the base portion of the mould cavity to the component portion 8 of the mould cavity. The crystals which grow fastest (generally those with the [001] direction aligned with the heat flow direction) are most likely to reach the entrance to the grain selector spiral first.

The spiral 7 acts as choke, reducing the number of crystals growing towards the exit of the spiral and the component portion 8 of the mould cavity above the spiral. When the process progresses correctly, a single crystal 13 of the desired crystallographic orientation (i.e with the correct [001] growth direction) emerges from the spiral 6 into the component portion 8 of the mould cavity.

As the solidification front advances up the cavity, the mould is withdrawn via baffle plates 9 into a cooled lower chamber 10, thus maintaining the thermal gradient and the epitaxial growth. The mould continues to be withdrawn until the single crystal has grown the entire length and width of the component portion 8 of the mould cavity.

Dendrites grow into the liquid metal at the solidification front between the liquid metal and solid metal. These dendrites are generally aligned with the direction of heat flow and so in the finished component will be aligned with the crystal planes (ie the <001> indices. However, in some cases, when secondary grains grow, the dendrites can have a different orientation (generally less than 20° from the component stacking axis).

As will become clear from the disclosure below, the method of the present invention makes use of this direct relationship between dendrite orientation and crystallographic orientation, by using interferometry to assess the orientation of the dendrite structure of a casting, and from that, calculating the crystallographic orientation.

In order to prepare a cast component for analysis by the method of the invention, the surface of the component is initially electrochemically etched so as to reveal the dendrite structure below. The resulting specimen 14 is then inserted into a retaining fixture 15, as illustrated schematically in FIG. 2, the fixture being configured to securely, but releasably, hold the specimen in place during analysis.

Figure 2:
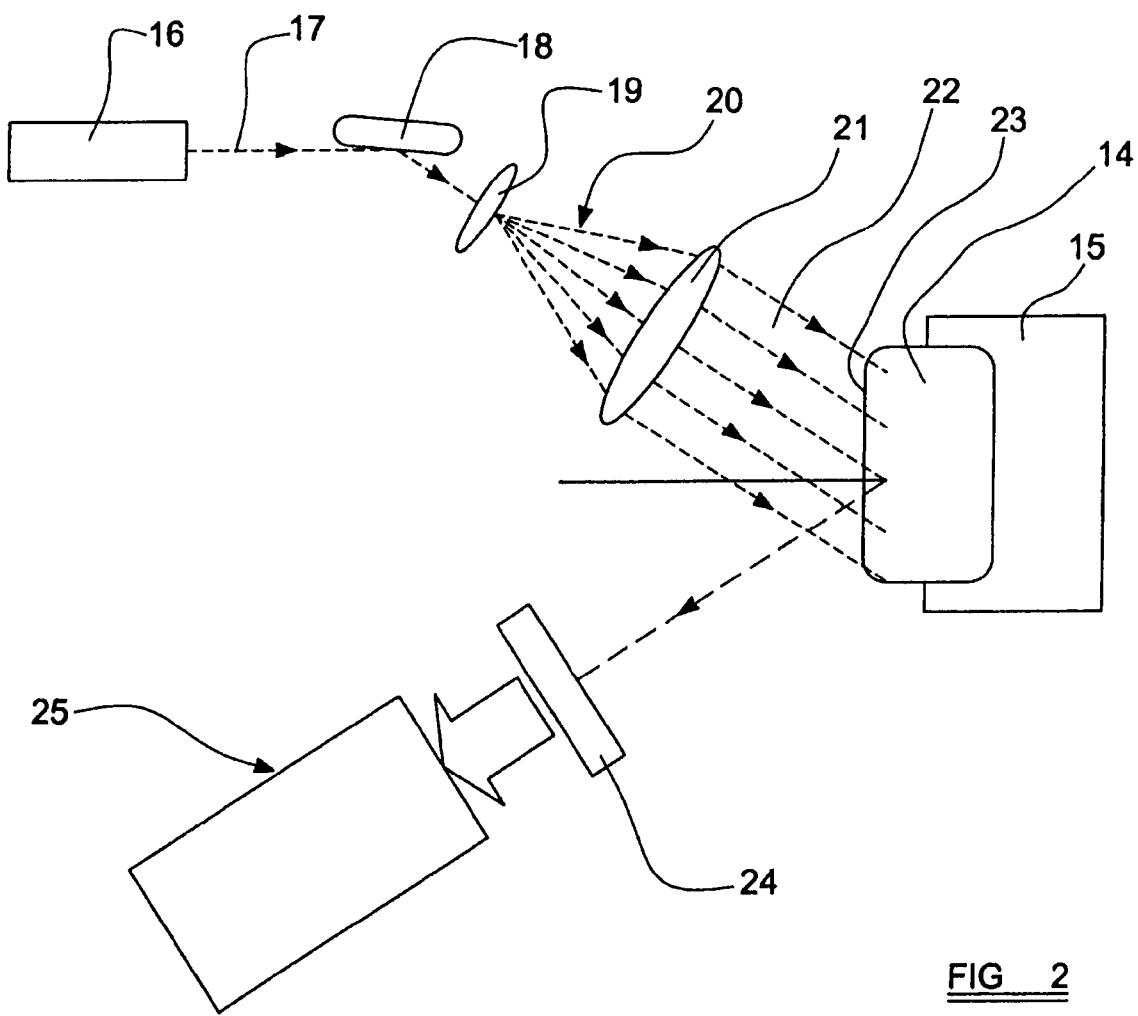
FIG. 2 shows the general arrangement of a system for implementation of the present invention.

The apparatus illustrated in FIG. 2 further comprises a LASER device 16 which serves as a source of coherent light which is used by the method of the present invention to provide observable interference effects. A narrow beam of light 17 is emitted from the laser device and is directed, by reflection in an external mirror 18, through a diverging lens 19. The diverging lens 19 serves as an expander to refract the narrow beam 17 into a diverging beam indicated generally at 20 in FIG. 2. A collimator 21 is positioned in the path of the diverging beam 20, the collimator 21 serving to produce a generally parallel beam of light 22, the parallel beam falling incident on the etched surface 23 with an acute angle of incidence a.

As illustrated schematically in FIG. 2, the light is reflected from the etched surface 23 of the specimen component 14 and a sensor 24 is arranged in the path of the reflected light. The light reflected from the component 14 has an interference pattern which depends on the orientation of the dendrites exposed by the etching on the surface 23 of the component.

The sensor 24 takes the form of an optoelectronic device such as a photodetector. The photodetector can take any convenient form such as a photoelectric cell or similar semiconductor device reactive to light falling incident on the device. The sensor 24 is configured to measure the mean angle and intensity of the scattered light reflected from the etched surface 23 of the component 14, and is electrically connected to a data processor device 25 which is configured to interpret the signals output by the sensor 24. The data processor comprises a memory containing information (for example in the form of a look-up table) from which the measured mean angle and intensity of the scattered light reflected from the etched surface 23 can be correlated to the crystal orientation of the sample in the [001] direction. It is envisaged that the data stored in the memory could be compiled from experimental analysis using the above-described interferometry method on a range of samples having known values of crystal orientation, in order to calibrate the apparatus.

In its broadest sense, the present invention should therefore be understood to be represented by a method for measuring the crystallographic orientation of a component via the steps of illuminating at least a region of the component surface with substantially coherent light, measuring the mean angle and intensity of the light reflected from the component surface and correlating said mean angle and intensity data to the crystallographic orientation of the component. The correlating step is performed by the data processor 25.

At this juncture, it should be appreciated that the interferometry method of the present invention, which is used to measure the crystallographic orientation of a component cast by a directional solidification process, differs from known laser-interferometry methods for measuring surface roughness of manufactured components. Such surface roughness measurement techniques make use of the fact that highly coherent light shone at a rough surface will be reflected from the surface in a scattered pattern by the peaks and troughs representing the surface roughness. The scattered light waves interfere and form an interference pattern consisting of a series of light and dark spots or speckles. The pattern of the resulting scattered light is then recorded using a CCD camera and a computer with a frame-grabber. The CCD camera and computer record an image of the scattered light pattern which is then analyzed using application-specific software in order to correlate the image with a value representative of the surface roughness of the component. In contrast to this method, it is to be noted that the method of the present invention includes the step of measuring the mean angle and intensity of light reflected from a component surface rather than actually recording an image of an interference pattern using a CCD camera or the like. This means that the method of the present invention allows the use of a much simpler sensor device with the result that the equipment becomes less susceptible to vibrations when compared to the use of a CCD camera. This means that the method of the present invention can be used more readily in a normal production environment where vibrations can be common.

Furthermore, it is to be noted that the method of the present invention lends itself particularly well to automation, largely as a result of the elimination of complex and delicate image recording equipment.

Figure 3:
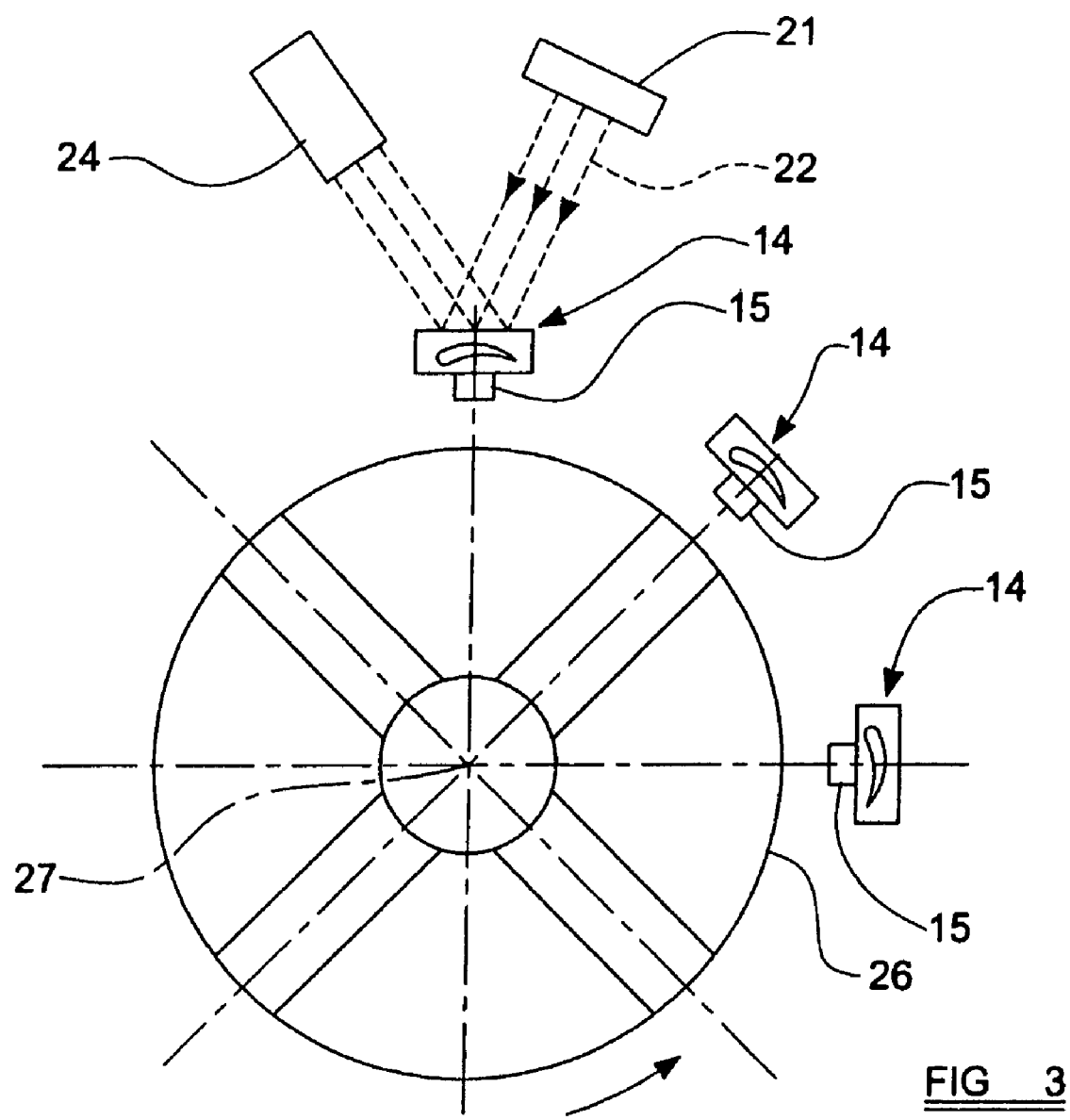
FIG. 3 shows an arrangement which may be used to at least partially automate the method of the present invention.

FIG. 3 illustrates in schematic form one possible configuration of apparatus for automated analysis of component parts using the method of the present invention. A carousel 26 is provided which is mounted for rotation about a central axis 27 between a series of discrete positions. At positions around the periphery of the carousel 27, the carousel is provided with a number of retaining fixtures 15, each of which is configured to securely, yet releasably, retain a respective specimen component 14 for analysis. In the arrangement illustrated in FIG. 3, the component 14 illustrated at the top of the drawing is located in a measuring position in which it is illuminated by a substantially parallel beam 22 of collimated light from a collimator 21, for reflection in the manner described above towards a sensor arrangement 24. When the component 14 has been analyzed according to the method of the present invention, the carousel 26 is rotated about its axis 27, for example under the action of a stepping motor, so as to move the analyzed component out of the measuring position and to move the next successive component around the periphery of the carousel into the measuring position ready for analysis.

Of course, whilst FIG. 3 illustrates an exemplary arrangement incorporating a rotatable carousel, it should be appreciated that the method of the present invention could be automated in other ways such as, for example, by use of a conveyor arrangement or the like.

The method can be further automated by the provision of an identifying barcode or other appropriate indicia on each component. The expansion apparatus can be provided with a barcode reader or the like to automatically read and hence identify individual components as they are analyzed. It is envisaged that the testing apparatus could be arranged automatically to update a material requirement planning (MRP) database in the event that any individual component is deemed to have an unacceptable crystal orientation. In the event that a non-conforming component is detected by the system, it is envisaged that the MRP database would be automatically updated and the component rejected. By updating the MRP database in this way, accidental release of defective parts into the manufacturing process can be avoided.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

The invention claimed is:

1. A method for measuring a crystallographic orientation of a component cast by a directional solidification process, the method comprising:
   generating coherent light with a laser;
   passing the coherent light emitted from the laser through a diverging lens and collimator to form substantially collimated and coherent light;
   illuminating at least a region of the component surface with the substantially collimated and coherent light;
   measuring a mean angle and intensity of light reflected from the component surface; and
   correlating the mean angle and intensity to the crystallographic orientation of the component.

2. A method according to claim 1, wherein the measuring comprises use of an optoelectronic device arranged such that the light reflected from the component surface falls incident upon the optoelectronic device.

3. A method according to claim 2, wherein the optoelectronic device comprises a photodetector.

4. A method according to claim 2, wherein the optoelectronic device is electrically connected to a processor, the processor being configured to perform the correlating.

5. A method according to claim 1, further comprising:
   etching at least the region of the component surface prior to illuminating the region, so as to expose a dendrite structure of the component in the region.

6. A method according to claim 5, wherein the etching involves electrochemical etching.

7. A method of measuring a crystallographic orientation of a plurality of components cast by a directional solidification process, the method being substantially automated and comprising:
   successively presenting each of the components for measurement in accordance with the method of claim 1.

8. A method according to claim 7, wherein the successively presenting comprises successively moving the components to a predetermined measuring location using a conveyor or carousel arrangement.

9. A method according to claim 7, further comprising:
   comparing the measured crystallographic orientation to a predetermined range of acceptable values, and rejecting an of the plurality of components having a crystallographic orientation outside the predetermined range.

10. A method according to claim 9, further comprising:
    comparing the measured crystallographic orientation to a predetermined range of acceptable values, and rejecting any of the plurality of components having a crystallographic orientation outside the predetermined range.

* * * * *